United States Patent
Donskoy et al.

(10) Patent No.: US 7,057,516 B2
(45) Date of Patent: Jun. 6, 2006

(54) DEVICE AND METHOD FOR DETECTING LOCALIZATION, MONITORING, AND IDENTIFICATION OF LIVING ORGANISMS IN STRUCTURES

(76) Inventors: Dimitri Donskoy, 48 Park La., Fair Haven, NJ (US) 07704; Michael Epstein, 1280 River Rd., Bedminster, NJ (US) 07921; Jaime A. Siegel, 1 Meadow La., Woodcliff Lake, NJ (US) 07677

( * ) Notice: Subject to any disclaimer, the term of this patent is extended or adjusted under 35 U.S.C. 154(b) by 0 days.

(21) Appl. No.: 11/091,163

(22) Filed: Mar. 28, 2005

(65) Prior Publication Data

US 2005/0168336 A1 Aug. 4, 2005

Related U.S. Application Data

(63) Continuation-in-part of application No. 11/028,396, filed on Jan. 3, 2005, which is a continuation-in-part of application No. 10/934,089, filed on Sep. 3, 2004, now abandoned, which is a continuation of application No. 10/309,489, filed on Dec. 3, 2002, now Pat. No. 6,801,131, which is a continuation-in-part of application No. 09/873,118, filed on Jun. 1, 2001, now abandoned.

(51) Int. Cl.
*G08B 23/00* (2006.01)

(52) U.S. Cl. ............................. 340/573.1; 340/545.3; 340/567; 43/124; 43/432.1; 324/637

(58) Field of Classification Search ............. 340/573.1, 340/539.23, 545.3, 567, 10.1; 43/124, 132.1, 43/107; 324/637, 639, 642; 119/721
See application file for complete search history.

(56) References Cited

U.S. PATENT DOCUMENTS

| | | | | |
|---|---|---|---|---|
| 4,809,554 A | * | 3/1989 | Shade et al. | 73/587 |
| 5,285,688 A | * | 2/1994 | Robbins et al. | 73/587 |
| 5,575,106 A | * | 11/1996 | Martin et al. | 43/132.1 |
| 5,877,422 A | * | 3/1999 | Otomo | 73/587 |
| 6,052,066 A | * | 4/2000 | Su | 340/870.16 |
| 6,150,944 A | * | 11/2000 | Martin et al. | 340/632 |
| 6,166,641 A | * | 12/2000 | Oguchi et al. | 340/573.1 |
| 6,255,652 B1 | * | 7/2001 | Moyer | 250/343 |
| 6,313,643 B1 | * | 11/2001 | Tirkel et al. | 324/642 |

* cited by examiner

*Primary Examiner*—Toan N. Pham
(74) *Attorney, Agent, or Firm*—Jaime A. Siegel, Esq.

(57) ABSTRACT

A device and method for detecting the presence of living organisms in a structure or behind a wall or partition utilizes a microwave or radio-frequency one or more transceivers which generate separate and distinct interrogating signals and receives separate and distinct signals reflected from a structure and living organisms within it. The reflected signals received by each of the transceivers are processed, for instance by a microprocessor, so as to provide output signals that indicate the presence or absence of a living organism in the structure or behind wall or partition. The microprocessor distinguishes and differentiate signals from different living organisms and from false indication of the presence of living organisms, thereby enabling the detection of living organisms despite the existence of motion signals caused by non-living organism motion. Similarly, the device can distinguish between the biological characteristics, such as respiration rates, of targets to determine if the targets are of the type sought, for example, human targets as opposed to pets or insects.

6 Claims, 10 Drawing Sheets

DEVICE AND METHOD FOR DETECTING LOCALIZATION, MONITORING, AND IDENTIFICATION OF LIVING ORGANISMS IN STRUCTURES

CROSS-REFERENCE TO RELATED APPLICATION

The present application is a continuation-in-part application of U.S. patent application Ser. No. 11/028,396, filed Jan. 3, 2005, which is a continuation-in-part application of U.S. patent application Ser. No. 10/934,089, filed Sep. 3, 2004, now abandoned which is a continuation application of U.S. patent application Ser. No. 10/309,489, filed Dec. 3, 2002, issued as U.S. Pat. No. 6,801,131, which is a continuation-in-part of U.S. patent application Ser. No. 09/873,118, filed Jun. 1, 2001, abandoned.

FIELD OF THE INVENTION

The present invention relates to a device and method for detecting living organisms, for example insects in or behind a structure and, more particularly, to a device and method for detection, localization, monitoring and identification of living organisms such as insects, animals, humans in or behind a structure or behind wall and other partitions, using interrogating signals, such as microwave or radio-frequency (RF) radiation, or acoustic broadcasting.

BACKGROUND OF THE INVENTION

An ability to detect, localize, and identify living organisms and monitor their activities has many uses. Biological attacks caused by wood destroying fungus, borers, termites, carpenter ants and the like are a major problem for structures made wholly or partially of wood. Such attacks can cause considerable damage to wooden structures. The detection and localization of active infestation of termites, ants, and other insects could substantially improve treatment outcome. The detection and monitoring of human activities gives the invention utility as a potential rescue system when it is used in the search for unconscious subjects who may be injured. The invention can also be used as intrusion and stowaway detection; it can help military forces clear a building when people may be concealed in interior hiding places. The invention will enable Special Weapons and Tactics (SWAT) or Special Operations Response Team (SORT) team commanders to better visualize hostage situations. Another equally important use of the invention is in law enforcement including police enforcement and management of correction institutions to detect and monitor offenders through structural walls.

Commonly used methods for detection of living organisms are mostly based on visual observations using human eyes or optical cameras. However if a partition obstructs the view visual approach does not work. Microwave, RF or acoustic signals can penetrate through a structure or partition thus offering an opportunity to detect living organisms within or behind it. This approach is known as Though Wall Sensing, or TWS. The sensing of living organisms' activities is based on their motion. The microwave, RF or acoustic TWS system is capable of detecting extremely small motions allowing for detection of living (moving) organisms in otherwise static environment. Conversely with the detection of insects in a wall, in the case where the invention is used to detect living organisms behind a structure or partition, the signals can be filtered to eliminate indications within a wall or structure to show the presence of living organisms on the other side of the structure or wall.

Prior art relevant to TWS are utilizing effects of Doppler or phase fluctuation due to motion of a target or echo-location of a target coupled with monitoring of target's position.

U.S. Pat. No. 3,754,254 to Jinman (the "Jinman '254 Patent") discloses a device for detecting moving targets by the Doppler shift of radiation reflected or scattered by a target that is illuminated by transmitted radiation. The Jinman '254 Patent focused on the problem of an interfering signal having a frequency difference from the transmitted radiation lying in the range of the expected Doppler shift, which would give a false target indication. The Jinman '254 Patent discloses that modulating the frequency of the transmitted radiation can mitigate such problem, so that the scattered or reflected radiation has a coherence with the transmitted radiation. The Jinman '254 Patent further discloses that a device performing the aforesaid function is particularly applicable to intruder alarm systems.

U.S. Pat. No. 6,313,643 to Tirkel (the "Tirkel '643 Patent") has been distinguished from the invention disclosed by the Jinman '254 Patent on the basis that the termite detection system disclosed therein includes a transmitter adapted to transmit a "near field" microwave signal into a structure and a receiver adapted to receive reflected signals that are indicative of the presence of insects in the "near field" of the microwave signal. However, the Tirkel '643 Patent does not disclose that the termite detection system is able to detect the presence of termites within the "far field" of the signal generated thereby. As a result, the termite detection system's function is substantially constrained. In addition, the Tirkel '643 Patent does not disclose whether the termite detection system is able to distinguish output signals indicative of the presence of termites in a structure and output signals caused by movement of the termite detection system itself. As a result, it would be difficult for an operator of the termite detection system disclosed by the Tirkel '643 Patent to distinguish false indications of the presence of insects in a structure from the actual presence of insects therein and, therefore, could lead to increased time and costs for testing a structure and/or inaccurate test results.

Recently developed TWS techniques to sense the location of a human subject inside of a room from the outside of that room is described in Hunt, A., Tillery, C., and Wild, N., "Through-the-Wall Surveillance Technologies," Corrections Today, Vol. 63, No. 4, July 2001. Thus, Greneker, et al. has developed so-called "RADAR Flashlight" which operates at X-band frequency range (near 10 GHz) and employs a CW homodyne radar configuration. (Greneker, E. F., "Radar Sensing of Heartbeat and Respiration at a Distance with Security Applications," Proceedings of the SPIE, Radar Sensor Technology II, Volume 3066, April 1997; Geisheimer, J. L., Marshall, W. S., and Greneker, E. F. "A continuous-Wave CW Radar for Gait Analysis," 35th IEEE Asilomar Conference on Signals, Systems and Computers, vol. 1, 2001, pp 834–838; Greneker, Geisheimer, J. "RADAR Flashlight Three Years Later: An Update on Developmental Progress," Proceedings of the 34th Annual International Carnahan Conference on Security Technology, Ottawa, Canada, October 2000).

Other reported developments are based on wide-band (pulse) technology working similar to echo-locating radars there presence and position of the target based on intensity and time-of-flight of reflected RF pulses. McEwan, T. E. "Ultra-wideband radar motion sensor", U.S. Pat. No. 5,361,070, discloses motion sensor based on ultra-wideband (UWB) radar technology. UWB radar range is determined by a pulse-echo interval. For motion detection, the sensors operate by staring at a fixed range and then sensing any change in the averaged radar reflectivity at that range. A sampling gate is opened at a fixed delay after the emission of a transmit pulse. The resultant sampling gate output is averaged over repeated pulses. Changes in the averaged sampling gate output represent changes in the radar reflectivity at a particular range, and thus motion.

Other prior art, Barnes et al., "Wide area time domain radar array" U.S. Pat. No. 6,218,979, describes a system and method for high resolution radar imaging using a sparse synchronized array of time modulated ultra wideband (TM-UWB) radars. Two or more TM-UWB radars are arranged in a sparse array. Each TM-UWB radar transmits ultra wideband pulses that illuminate a target, and at least one receives the signal returns. The signal return data is processed according to the function being performed, such as imaging or motion detection.

There is other prior art that utilizes a synchronized array of transmitters and/or receivers for coherent processing of reflected signals, such as described by Geisheimer, et al., Phase-based sensing system, U.S. Pat. No. 6,489,917.

Although significant resources have been devoted to development of practical and commercially viable TWS systems, so far these efforts produced mostly demonstrational or experimental prototypes which are difficult and impractical to employ for real world applications. One of the reasons is that none of the referred prior art is able to distinguish one type of living organism from another: for example to distinguish termite related activity in a wall from moving people that pass behind the same wall. The prior art can't differentiate between insect and human.

In addition, there is no known-living organisms detection device that is able to distinguish motion signals indicative of the presence of living organisms in a structure and signals caused by movement of the device itself. Since electronic insect detection devices typically contain sensitive components designed to detect the movement of insects, any movement of these devices can lead to the false indication of the presence of living organisms in a structure. For instance, hand tremors of an operator holding a living organism detection device cause significant movement thereof. In addition, if a living organism detection device is placed against a structure to be tested, structural vibrations caused by wind, appliances or nearby moving vehicles can lead to the movement of the detection device. Also, moving vehicles that pass behind a structure undergoing testing can cause motion signals that can lead to false indications of the presence of living organisms in a structure. As a result, it would be difficult for an operator of a living organism detection device to distinguish false indications of the presence of living organisms in a structure from the actual presence of living organisms therein.

Accordingly, what would be desirable, but has not yet been developed, is a reliable practical device and method for detecting, localization, monitoring, and differentiating living organisms inside structures, within or behind walls and other partitions.

SUMMARY OF THE INVENTION

In accordance with the present invention, a living organism detection, localization, monitoring, and identification device and method employ a plurality of transceivers, each of which generate separate and distinct interrogating signals and receives separate and distinct signals reflected from a structure being tested for presence of living organisms. The reflected signals received by each of the transceivers are processed, for instance by a microprocessor, so as to provide output signals that indicate the presence or absence of living organisms in the structure being tested.

It is another object of the present invention to provide a method and apparatus for the detection, localization, monitoring, and identification of living organisms in dwellings, other structures, and behind walls, doors, or other partitions while being outside of the structures or on the other side of a partition.

It is another object of the present invention to provide a method and apparatus for the detection, localization, monitoring, and identification of living organisms in dwellings, other structures, and behind walls, doors, or other partitions that can be easily be placed into operation by a user.

It is another object of the present invention to provide a method and apparatus for the detection, localization, monitoring, and identification of living organisms in dwellings, other structures, and behind walls, doors, or other partitions where the type of material that the walls, doors or other partitions are constructed of can be manually set by an operator or automatically detected by the apparatus.

It is another object of the present invention to provide a method and apparatus for the detection, localization, monitoring, and identification of living organisms in dwellings, other structures, and behind walls, doors, or other partitions utilizing an antenna that is capable of adjusting its impedance.

It is another object of the present invention to provide a method and apparatus for the detection, localization, monitoring, and identification of living organisms in dwellings, other structures, and behind walls, doors, or other partitions that can measure the thickness of the walls, doors or other partitions.

It is another object of the present invention to provide a method and apparatus for the detection, localization, monitoring, and identification of living organisms in dwellings, other structures, and behind walls, doors, or other partitions with an adjustable reference threshold based on the type of wall, door or other partition.

It is yet another object of the present invention to provide a method for detection, localization, monitoring, and identification of living organisms in dwellings, other structures, and behind walls, doors, or other partitions with high sensitivity and a low rate of false alarms.

It is an additional object of the present invention to provide a method and apparatus for detection, localization, monitoring, and identification of living organisms in dwellings, other structures, and behind walls, doors, or other partitions while being outside of the structures without being in close proximity to the structure or partition.

The method and the apparatus of the present invention are comprised of one or a plurality of independent interrogating sensors. The sensors can be standalone, i.e. performing interrogation, data acquisition, processing and displaying, or could be wired or wirelessly communicating with one or a plurality of independent communication modules, a signal processor for extracting information relevant to a living organisms' (targets) activities and suppressing unrelated interfering signals, and a data processing/displaying module for displaying information about targets' activities and their location as well as controlling sensors' operation. Among the information that may be extracted is information regarding the vital signs of the target.

A wireless link between sensor and data processing/displaying module allows the ability to provide a safe stand-off distance for an operator, create light weight, low cost reusable or even disposable sensors requiring minimum battery power. Another benefit of wireless connectivity is an ability to deploy various sensor delivery means, so sensor could be easily placed or attached with adhesives on wall surface, thrown with a hand or mechanical means as projectile, or delivered with a robotic device. Yet another extremely important benefit of the wireless connectivity is elimination of sensor motion caused by operator hand or body tremor.

By providing a plurality of sensors, the present invention allows a user to determine the position of a target using triangulation or observing signal intensity changes from sensor to sensor as a target moves inside a structure. A plurality of sensors also helps to eliminate certain types of false indications of the presence of living organisms in a structure. For example, structural vibrations could cause all sensors attached to the structure to indicate presence of motion approximately the same intensity, which unlikely to take place if sensor's motion signal outputs are caused by a living organism situated at different distances and/or angles with respect to different sensors. A plurality of sensors allow for implementation of more sophisticated signal processing algorithms so the data from various independent sensors could be processed collectively further reducing false indication of living organisms presence and their activities.

The various configurations of the system provide the following advantages:
- Eliminates self-motion effects because of fixed position of the interrogating sensors
- Provides freedom of motion and safe distance/location for an operator such as soldier, policeman, or rescuer
- Allows for simple one handed placement against a partition.
- Allows for ample time for safe data gathering and reliable detection
- Provides simultaneous detection at multiple locations (eventually covering the entire structure)
- Enables advanced multi-channel processing algorithms for elimination of false alarms
- Allows for information shearing between soldiers, commanders, etc.
- The system operates in various modes providing flexibility and affordability for various users.

Further features and advantages of the invention will appear more clearly on a reading of the detailed description of the exemplary embodiments of the invention, which are given below by way of example only with reference to the accompanying drawings.

BRIEF DESCRIPTION OF THE DRAWINGS

For a better understanding of the present invention, reference is made to the following detailed description of the exemplary embodiments considered in conjunction with the accompanying drawings, in which.

DETAILED DESCRIPTION OF THE DRAWINGS

The present invention relates to a device and method for nondestructive detection, localization, identification, and monitoring of living organisms inside structures, within or behind walls and other partitions using penetrating interrogating signals such as microwave, RF or acoustic radiation. By structures it is meant any structure, including, but not limited to, houses, buildings, containers, compartments, bridges, other wooden, concrete or metal structures, wooden or metal frames, utility poles, piles, etc. The detection of living organisms is based on their reflectivity and/or constant motion. For example, all living organisms are comprised of electrolyte (conductive) material while many construction materials such as wood, sheetrock, and others are dielectric. This creates high contrast reflectivity for microwave and RF radiation. Living organisms are made out of water and other substances much denser than air thus creating high reflectivity for acoustic waves propagating in air. Also, all living organisms are in constant motion. The present invention detects very small movements (fraction of mm per second), thus allowing for detection of living (moving) organisms in static material.

Figure 1:
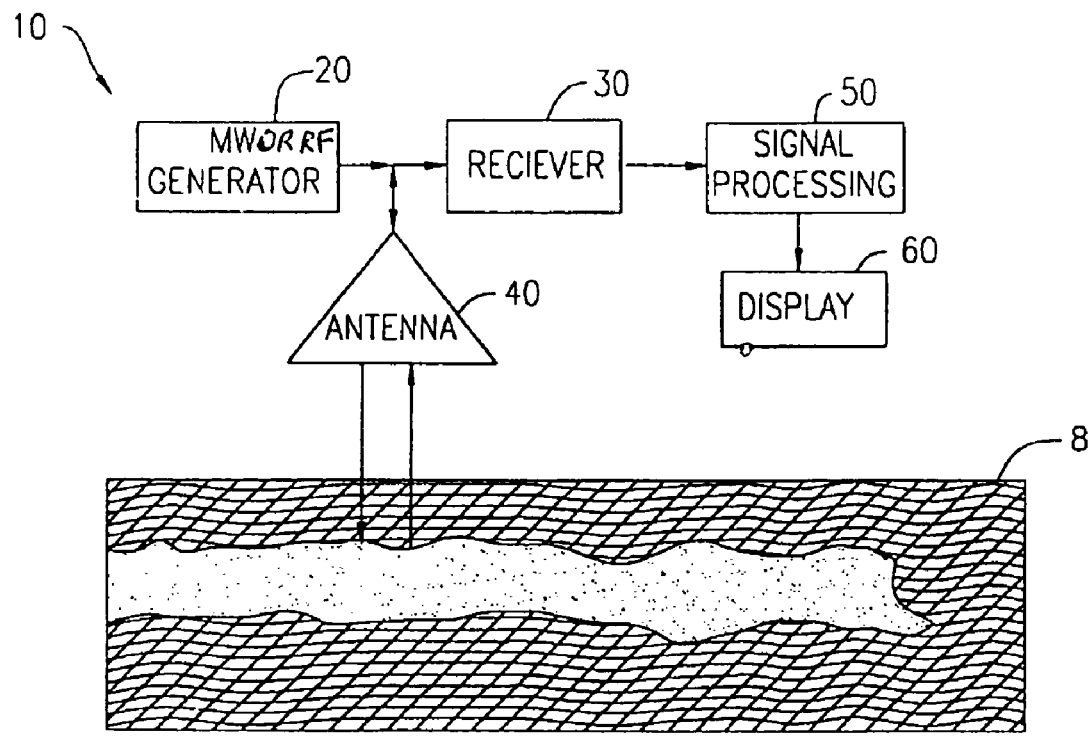
FIG. 1 is a block diagram of a living organism and damage detection device in accordance with an exemplary embodiment of the present invention.

As can be seen in FIG. 1, the apparatus of the present invention, generally indicated as 10, includes a microwave or RF generator 20, a receiver 30, an antenna 40 for sending and receiving signals, a signal processor 50 for processing the received signals and a display 60. Preferably, the apparatus is hand-held and is moved along the wooden structure 8 being tested. Microwave or RF signals (i.e., radiation) are generated by the generator 20. The generator 20 does not have to be particularly strong; for example, in testing it was found that a 10 mW generator was sufficient. The generated signal is constantly sent by the antenna 40, which also constantly receives a reflected signal. The signals are received by the receiver 30 and processed by the signal processor 50. Optionally, the apparatus 10 can include the display 60 for displaying the results. Alternatively, the apparatus 10 could merely emit an audio or visual alarm indicating the presence of live organism. Alternatively, the generator 20 may generate acoustic signals having power level of a few watts.

The method includes generating and sending a microwave, RF or acoustic signal, receiving a reflected signal, and processing and evaluating the received signal. It has been found that a generated microwave or RF signal having a frequency of between 0.5 and 50 Ghz is suitable; acoustic signal having frequency of between 1 KHz–200 kHz is suitable for TWS. The method could be employed with a hand-held unit wherein the unit is moved about a structure to be tested. Alternatively, the apparatus could be stationary and allowed to operate for a given time to cover a given area. In such a case, the apparatus could be attached to the wooden structure being tested for a short period of time, or left attached for a longer time for long term monitoring.

The apparatus 10 could additionally include a stimulator for stimulating living organisms' movement to make detection easier (not shown in FIG. 1). The stimulator could be based on vibration, ultrasound, electromagnetic radiation, heating, etc. Preferably, a stimulator would be used prior to or during the application of the probing device.

An exemplary application of the invention was conducted. In the example, tests were performed with live ants contained within a plastic box and dead ants which were attached to an adhesive. The ants were placed beneath a wooden board.

Figure 2:
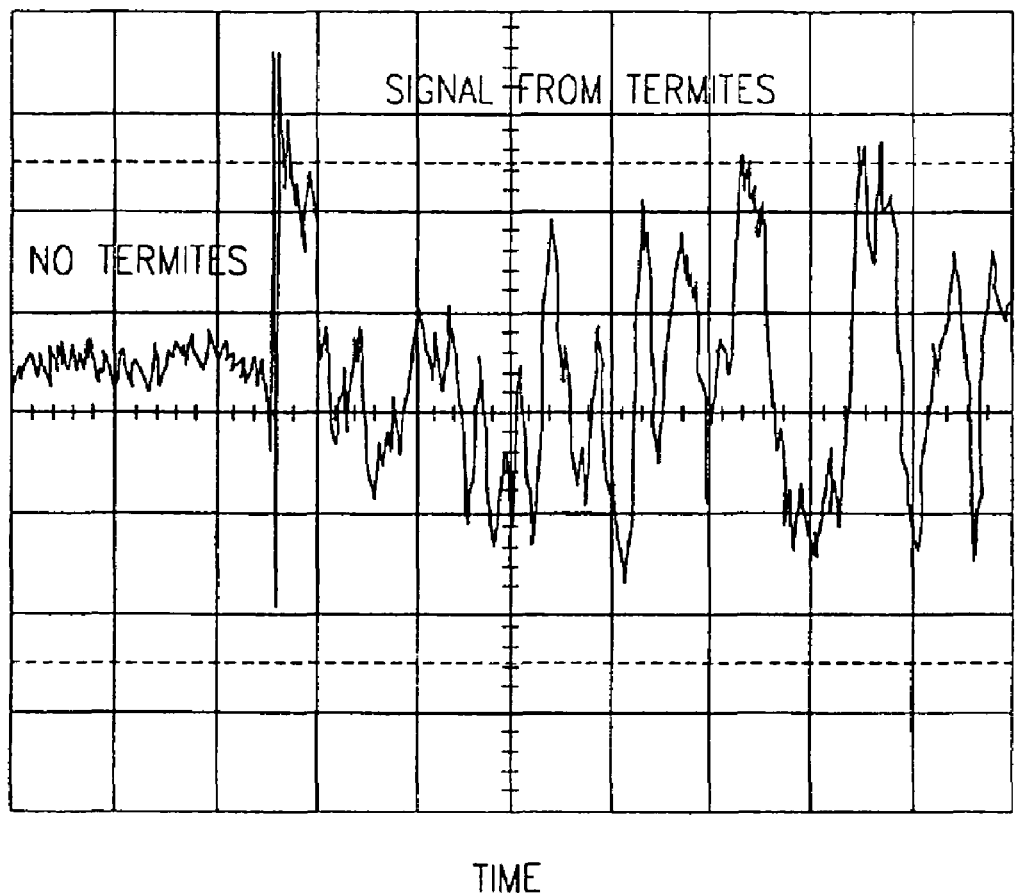
FIG. 2 is a graph of an output signal of the living organism and damage detection device shown in FIG. 1, which shows both the absence and presence of live organisms.

As shown in FIG. 2, where there is no motion, i.e. dead ants, there is basically no output signal from the probe. However, slight motion of live insects resulted in appreciable output signals.

In another exemplary case, live termites were put into a plastic container and one-inch wood board was used to separate the probe from the container. A significant output, similar to that shown in FIG. 2 (but not shown in the Figures), was achieved for live termites as opposed to the absence of termites.

Figure 3:
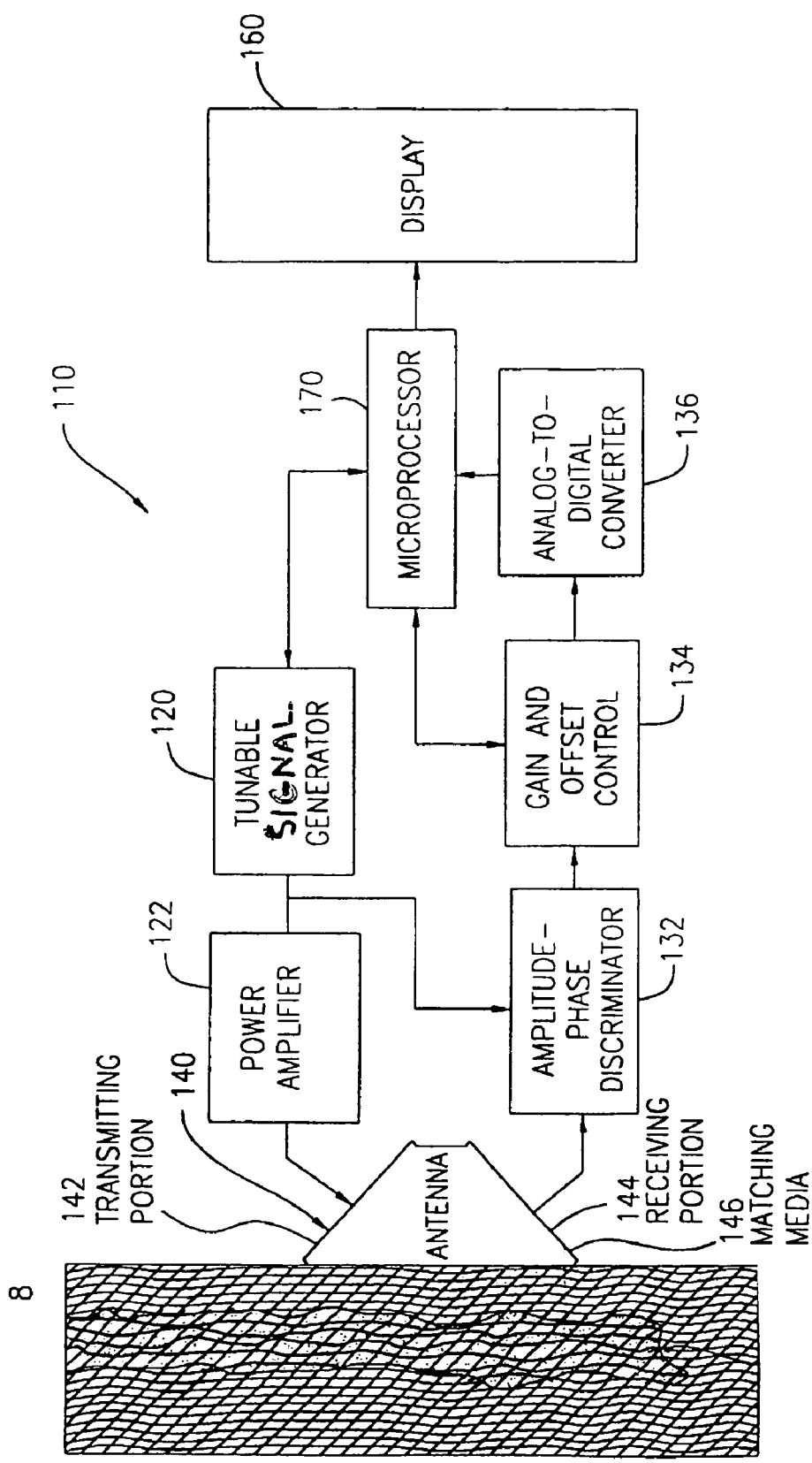
FIG. 3 is a block diagram of a living organism and damage detection device in accordance with a second exemplary embodiment of the present invention.

FIG. 3 shows another embodiment of the present invention generally indicated as 110. The device includes an antenna 140 having a transmitting portion 142 and a receiving portion 144. The transmitting and receiving portions 142, 144 can be interconnected with a circulator (not shown in FIG. 3). Alternatively, two separate transmitting and receiving antennas can be utilized. The transmitting portion 142 of the antenna 140 radiates the tested structure 8 with probing microwave, RF or acoustic energy. The transmitted energy penetrates into/through the tested structure 8 via matching media 146 having similar properties to stranture's dielectric or acoustic properties. Inhomogeneities in and behind the structure, such as insects or other living organisms, cause reflection of the interrogating signal back to the receiving portion 144 of antenna 140. The received signal is processed for moving living organism detection. A tunable signal generator 120 is controlled by a microprocessor 170. The tunable signal generator 120 interconnects with a power amplifier 122 to deliver a signal to the antenna 140. The receiving portion 144 of antenna 140 outputs a signal to an amplitude and phase discriminator 132 that is interconnected with the tunable generator 120. The signal is then sent to a gain and offset control 134 which is interconnected with the microprocessor 170 and then sent to an analog-to-digital converter 136 and then to the microprocessor 170. Finally, the output is displayed on a display 160.

In the calibration mode, the microprocessor 170 sweeps the frequency range of the generator 120 to find a frequency with maximum (strongest) received signal. In the detection mode, the microprocessor 170 sets the fixed frequency of the generator 120. This frequency corresponds to the maximum received signal, for greatest sensitivity. If there are moving reflectors (i.e., living organisms) the received signal contains amplitude and phase variations due to the motion. These variations are extracted with the amplitude-phase discriminator 132 and sent to the gain and offset control device 134, which adjusts amplification and offset voltage for optimum evaluation of the signal sent to the microprocessor 170. The microprocessor 170 calculates the standard deviation of the received signal. When deviation exceeds a threshold level, predetermined during sensor calibration, the microprocessor 170 sends a live insect message to the display 160. The display can be a simple indicator, i.e. a red, green indicator, a sound indicator, or a more sophisticated LED or LCD display.

Figure 4:
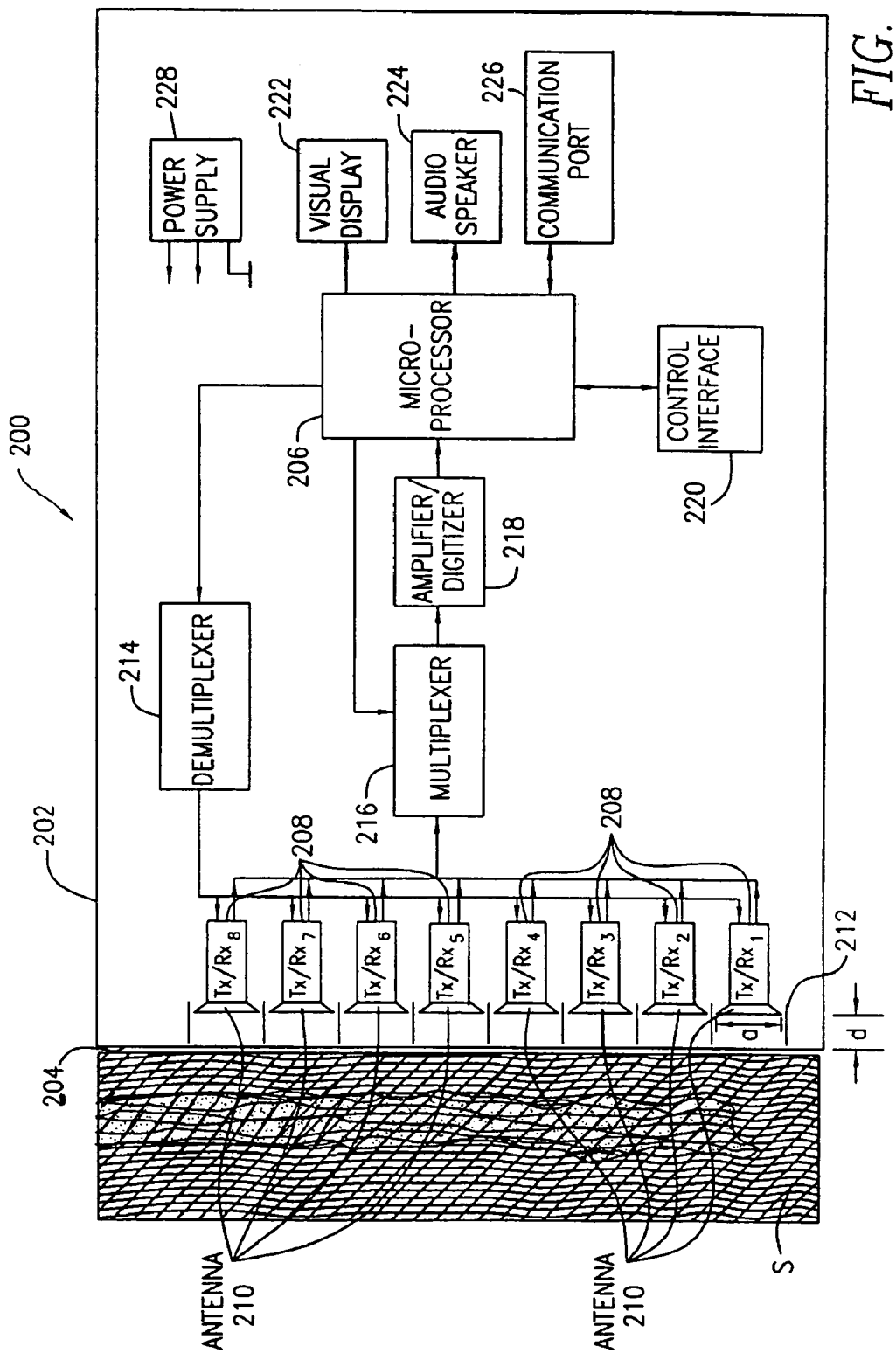
FIG. 4 is a block diagram of a living organism and damage detection device in accordance with a third exemplary embodiment of the present invention.
Figure 6:
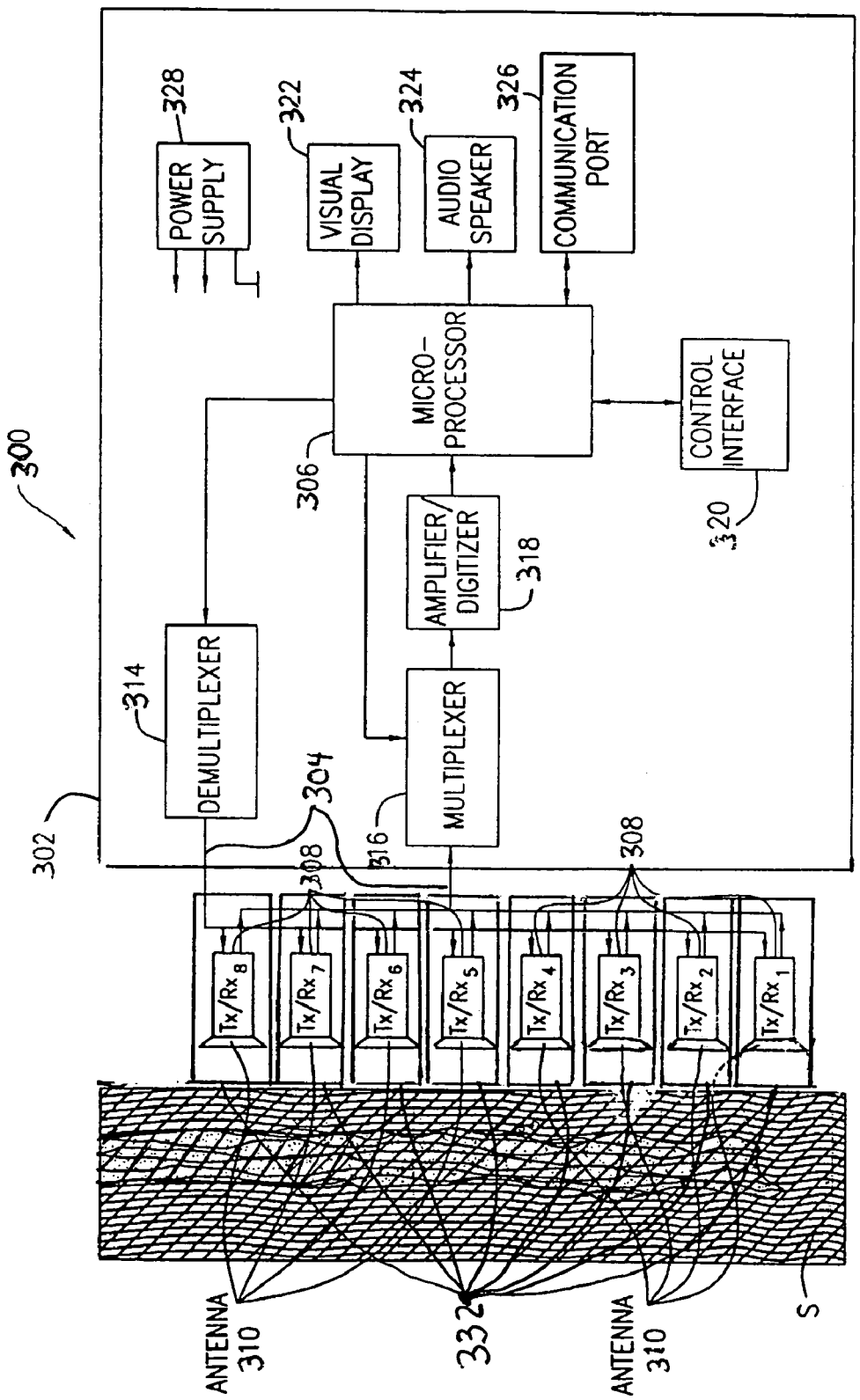
FIG. 6 is a block diagram of a living organism and damage detection device in accordance with a fourth exemplary embodiment of the present invention

Another exemplary embodiment of the present invention is illustrated in FIG. 4, wherein a living organism detection device 200 includes a rectangular-shaped housing 202 having an end 204, a microprocessor 206 and eight (8) transceivers 208 that are positioned proximate to the end 204 of the housing 202. The housing 202 supports and houses the other components of the living organism detection device 200, and is preferably rectangular in shape, but it can consist of other shapes and sizes. The living organism detection device 200 preferably includes the eight transceivers 208, but it may include a greater or lesser number than eight. Furthermore, the transceivers 208 are preferably positioned linearly proximate to the end 204 of the housing 202 (as shown in FIG. 4), but other configurations of the positioning of the transceivers 208 may be utilized. For example, as shown in FIG. 6, the transceivers 308 may be separated from the main housing 302 and connected to the main housing 302 by a cable or bus 304. The transceivers 208 are sometimes collectively referred to herein as "channels" and each individually as a "channel." The functions of the microprocessor 206 and the transceivers 208 shall be described hereinafter.

Still referring to FIG. 4, each of the transceivers 208 has a corresponding antenna 210 connected thereto and whose function shall be described hereinafter. In the case that the living organism detection device 200 is intended to detect living organisms very close to the device, for example insects in a wall, it is important that each of the antennas 210 is located at a specifically selected distance "d" from the end 204 of the housing 202 (as shown in FIG. 4), whereby the distance "d" is greater than the "near field" of the signals transmitted by the antenna 210. The near field of the signal transmitted by each of the antennas 210 is defined as a distance equal to or lesser than twice the square of its aperture width divided by the wavelength of the signal transmitted thereby, i.e., near field # $2a^2/\lambda$, whereby "a" is the aperture width of the antenna 210 (as shown in FIG. 4) and $\lambda$ is the wavelength of its transmitted signal. Each of the antennas 210 is preferably a horn antenna, but any or all of the antennas 210 can consist of a microstrip antenna, a dish antenna, or any other type of suitable antenna. Each of the antennas 210 and its corresponding transceiver 208 are flanked by rectangular-shaped partitions 212 (only one of which is labeled in FIG. 4 with reference number 212) whose functions shall be described hereinafter. Furthermore, it is desirable, although not required, that the antennas 210 be selected with impedance that is matching electromagnetic impedance of the wall. For example, an antenna with a high dielectric constant may be used when the wall to be scanned is made of concrete, which also has a high dielectric constant. Each of the partitions 212 is preferably rectangular in shape and manufactured from a conductive material such as aluminum, but they can consist of other shapes and sizes and/or manufactured from other materials. The living organism detection device 200 can include a rectangular-shaped covering (not shown in FIG. 4), preferably manufactured from a conductive material such as aluminum, that covers the top of the partitions 212, and which, together with the partitions 212, substantially enclose each of the antennas 210.

The living organism detection device 200 can also be used to detect living organism targets 230 on the other side or at a distance from the other side of a structure, wall or partition. In this case, because the living organism target 230 is not so close to the antennas 210, the distance "d" is not as critical because the living organism target 230 most likely will be in the far field of the signal transmitted by antennas 210. Therefore, in an embodiment intended to detect living organism targets 230 through a structure, wall or partition, rather that within it, the antennas 210 can be positioned at any distance from the end 204.

Still referring to FIG. 4, the living organism detection device 200 further includes a demultiplexer 214 and a multiplexer 216, each of which are electrically connected to and controlled by the microprocessor 206 and whose functions shall be described hereinafter. The transceivers 208 are electrically connected to the demultiplexer 214 in parallel. Similarly, the transceivers 208 are electrically connected to the multiplexer 216 in parallel. The living organism detection device 200 further includes an amplifier/digitizer 218 that is electrically connected to the multiplexer 216 and the microprocessor 206 and whose function shall be described hereinafter. A control interface 220, a visual display 222, an audio speaker 224 and a communication port 226 are each electrically connected to the microprocessor 206, and the functions of which shall be described hereinafter. A power supply 228 provides electrical power to all of the aforesaid electronic components of the living organism detection device 200.

It is noteworthy that the microprocessor 206 is preferably manufactured by Amtel Corporation and having a model number of ATMega-16AC, while each of the transceivers 208 is preferably manufactured by Microwave Device Technology Corporation and has a model number of MO9061. In addition, each of the antennas 210 is preferably manufactured by Microwave Device Technology Corporation and has a model number of MHA4137. The demultiplexer 214 and multiplexer 216 are each preferably manufactured by Texas Instruments, each having a model number of CD4051. Alternatively, the aforesaid components may be manufactured by other entities and/or different models of such components may be utilized.

Still referring to FIG. 4, the living organism detection device 200 operates in the following manner. Each of the transceivers 208 generates microwave, RF or acoustic signals that are separate and distinct from the signals generated by each of the other transceivers 208. The signals generated by each transceiver 208 are transmitted by its corresponding antenna 210 into a portion of a structure S to be tested (as shown in FIG. 4) such as a wall, ceiling, floor, etc. Each of the antennas 210 and, in turn, its corresponding transceiver 208, receives reflected signals from the structure S. The reflected signals received by each of the antennas 210 and its corresponding transceiver 208 are separate and distinct from the reflected signals received by each of the other antennas 210 and its corresponding transceiver 208. It is preferable that each of the transceivers 208 has a single corresponding antenna 210 connected thereto that both transmits interrogating signals generated by the transceiver 208 and receives reflected signals to be received by the transceiver 208. Alternatively, each of the transceivers 208 may have a pair of corresponding antennas connected thereto, whereby one antenna transmits the signals generated by the transceiver 208, while the other antenna receives the reflected signals to be received by the transceiver 208.

The microwave or RF signal generated by each of the transceivers 208 is not required to be powerful. For example, a 10 mW microwave/RF signal having a frequency within the range of 0.5 to 50 GHz is sufficient for the operation of the living organism detection device 200. Alternatively, the transceivers 208 may generate acoustic signals to be transmitted by antennas 210. A few watts acoustic signal generated within the frequency range 1 kHz to 200 KHz is sufficient for the operation of the detection device 200 transmitting acoustic energy. However, microwave, RF or acoustic signals generated with different levels of power and/or having different frequencies can be utilized. The demultiplexer 214, which is controlled by the microprocessor 206, sequentially activates and sequentially deactivates each of the transceivers 208, whereby the transceivers 208 are activated and deactivated in succession. In other words, only one of the transceivers 208 generates signals and receives reflected signals from the structure S at a particular time. For example, the demultiplexer 214 activates one of the transceivers 208 (for instance, the transceiver 208 labeled as "Tx/Rx$_1$" in FIG. 4), which generates signals and receives the reflected signals for a short period of time, while at the same time, the other seven transceivers 208 (labeled as "Tx/Rx$_2$" though "Tx/Rx$_8$" in FIG.4) remain deactivated. Next, the demultiplexer 214 simultaneously deactivates the activated transceiver 208 (i.e., the transceiver 208 labeled as "Tx/Rx$_1$" in FIG. 4) and activates another one of the transceivers 208 (preferably the transceiver 208 that is next in line, which is labeled as "Tx/Rx$_2$" in FIG. 4), which generates microwave signals and receives reflected signals for a short period of time. During this time, the other seven transceivers 208 (labeled as "Tx/Rx$_1$" and "Tx/Rx$_3$" though "Tx/RX$_8$" in FIG.4) remain deactivated. The demultiplexer 214 activates and deactivates each of the transceivers 208 in succession and, thereafter, the cycle is repeated. Alternatively, all of the transceivers 208 may remain continuously activated.

Still referring to FIG. 4, the partitions 212 shield the antennas 210 from each other, thereby reducing any interference between the signals transmitted by the antennas 210 and between the reflected signals received thereby. The partitions 212 also shield the antennas 210 from signals that are reflected by portions of a structure that are not, at that particular time, subject to testing. For example, if a front wall of a structure is subject to testing, signals are reflected from the front wall as well as, for instance, sidewalls of the structure. Consequently, the signals reflected from the sidewalls of the structure can cause interference with the signals reflected from the front wall of the structure, i.e., the portion of the structure subject to testing. Thus, the partitions 212 shield the antennas 210 from signals reflected from the sidewalls of the structure being tested, thereby reducing or eliminating interference with the signals reflected from the front wall of the structure. Finally, the partitions 212 shield the antennas 210 from extraneous sources of electromagnetic radiation, e.g., television stations, radars, etc. As previously noted, the living organism detection device 200 can include a rectangular-shaped covering (not shown in FIG. 4), preferably manufactured from a conductive material such as aluminum, that covers the top of the partitions 212, which, together with the partitions 212, substantially enclose the antennas 210, and further shields the antennas 210 from each other, from signals that are reflected by portions of a structure that are not, at that particular time, subject to testing and from signals generated by extraneous sources.

The multiplexer 216, which is controlled by the microprocessor 206, receives and interrogates the reflected signals received by each of the transceivers 208. The reflected signals received by the multiplexer 216 are then amplified and digitized by the amplifier/digitizer 218, which allows for the reflected signals' data to be processed and analyzed by the microprocessor 206 in order to provide output signals that indicate the presence or absence of living organisms in the structure S or behind the structure S, noted as target 230.

When moving living organisms, such as termites, ants, human or others are present in or behind the structure S, their motion causes low frequency modulation of the reflected signals received by each of the antennas 210 its corresponding transceiver 208. The modulating frequencies of the reflected signals are typically less than 10 Hz. The modulated, reflected signals and a portion of the transmitted signals are mixed within each of the transceivers 208 so as to produce low frequency difference signals, which are indicative of motion. Since the modulated frequency of the reflected signals (when living organisms are present) are typically less than 10 Hz, the reflected signals received by each of the transceivers 208 are sampled at a rate greater than 10 Hz, for example 256 Hz. The acquisition time "$\theta$" to acquire a data sample for a channel (i.e., a single transceiver 208) is preferably less than or equal to $1/(N \times F)$, where N is the number of channels (i.e., the number of transceivers 208) and F is the sampling rate in Hz. The reflected signals received by each channel is subsequently interrogated by the multiplexer 216 to produce data sample streams $D_n$ ($d_{nm}$), where "n" is a channel number, "m" is a sample number and "d" is a single bit of data. The reflected signals have different characteristics, or "signatures", depending on the living organism. For example, signals from insects are non-deterministic, that is, the output signals processed therefrom would be visualized as "noise." Accordingly, the data processing and analysis conducted by the microprocessor 206 consists of calculating the moving average for each data stream $D_n$ and determination of the signal deviation indicative of a positive motion signal. The deviation could be determined by the differentiation, the calculation of signal dispersion and other similar procedures known on the art of signal processing. The deviation is compared with a predetermined threshold. If the deviation exceeds the predetermined threshold, then the audio speaker 224 will issue an audible alarm. The greater the movement of insects, the greater the deviation and the higher the pitch of the sound generated by the audio speaker 224. A proximity switch may also be used, such that signals are not transmitted by the antenna 210 until the detection device 200 is position next to the interrogating wall.

Very often, however, the signal deviation could be caused by motion of the detection device 200 itself. For instance, hand tremors of an operator holding the detection device 200 while testing the structure S, structural vibrations (caused by wind, appliances, etc.) or moving vehicles passing behind the structure S could cause motion signals, thereby resulting in a signal deviation that exceeds the predetermined threshold. This would lead to the false indication of the presence of insects in the structure S, i.e., non-insect motion, and, consequently, "false alarms" produced by the audio speaker 224 could occur. In this regard, the plurality of transceivers 208 plays a fundamental role to discriminate between the false indication of the presence of insects in the structure S (i.e., non-insect motion) and the actual presence of insects in the structure S. Since most insects, such as termites, ants, etc. move along narrow paths, only one or a couple of the transceivers 208 will detect the insects' motion, while the remaining transceivers 208 will not detect the insects' motion. If a condition that would trigger a false indication of the presence of insects in the structure S occurs (i.e., hand tremors, structural vibrations, moving vehicles etc.), all, or substantially all, of the transceivers 208 will receive a positive motion signal that indicates the possible presence of insects in the structure S, which is a false indication of the presence of insects in the structure S.

The microprocessor's 206 signal-processing algorithm is written to take into account the occurrence a false indication of the presence of insects in a structure. For example, if all or most of the transceivers 208 receive a positive signal (i.e., a motion signal) that indicates the possible presence of insects in the structure S, the microprocessor 206 will process these positive signals to determine whether they are substantially similar to each other. If the positive signals (i.e., motion signals) are substantially similar to each other, then the microprocessor 206 will extract the common positive signal received by the transceivers 208 and subtract such common positive signal from all of the signals received by the transceivers 208, thereby generating residual signals. The residual signals are then analyzed to determine the presence of insects. Therefore, the insect detection device 200 is able to detect the presence of insects in the structure S despite the existence of motion signals caused by non-insect motion.

Similarly, if the living organism detection device 200 is intended to detect living organism targets 230 through a structure S, wall or partition. This situation is more relevant to detection of humans or animals. Signals, reflected from human or animals contain both noise-like (random motion) and deterministic (respiration, heartbeat) components. Still, these signals are non-stationary and nonlinear. As a result, conventional signal processing techniques such as Fourier transforms or statistical techniques such as described above are not very useful in differentiation between different "signatures". The microprocessor's 206 signal processing algorithms can be programmed for more sophisticated algorithms such as empirical mode decomposition, adaptive filtering, and others known in art of advanced signal processing techniques to extract "signatures" relevant to various organisms. Here again the plurality of transceivers 208 plays an important role to avoid the false detection that may be generated by non-living organism motion of the structure S or transceivers themselves.

Figure 9:
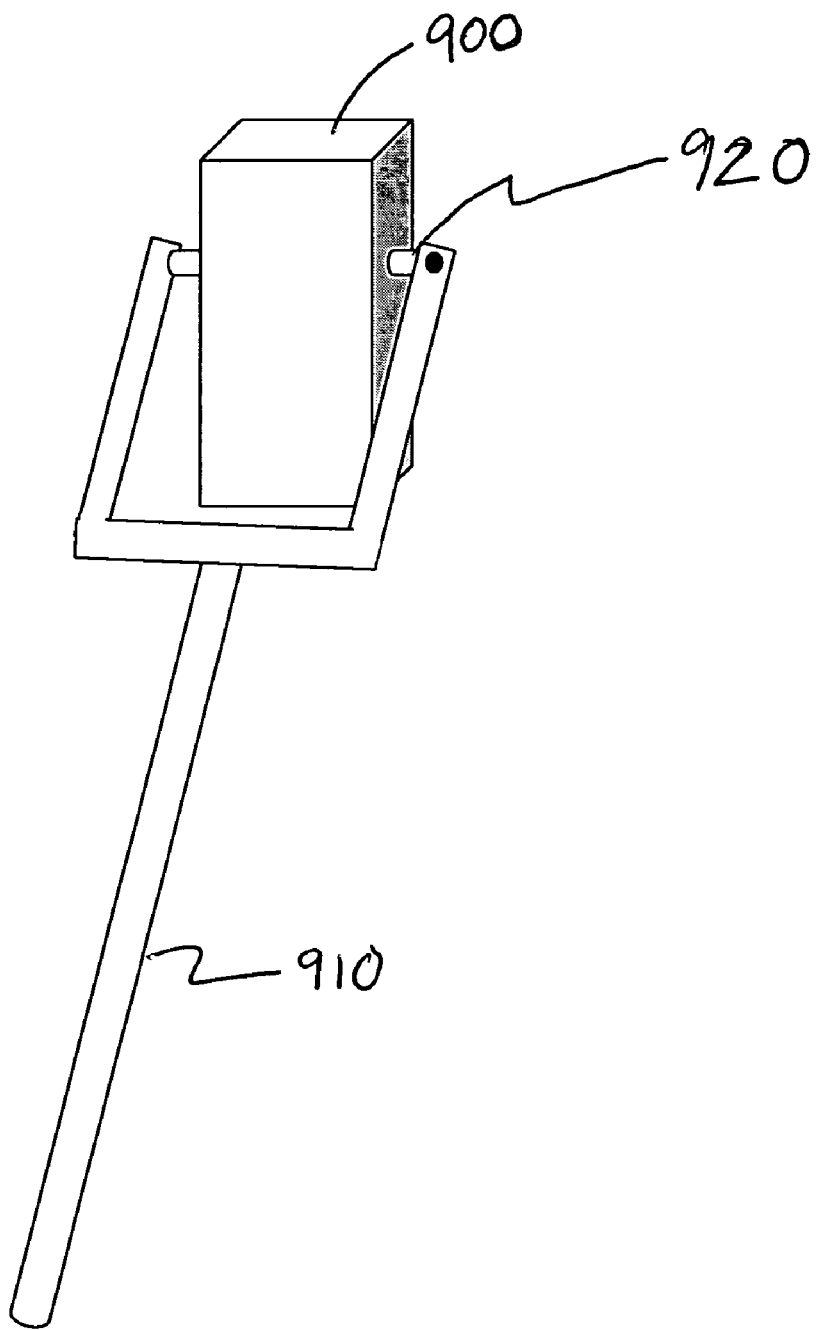
FIG. 9 is a diagram of a living organism and damage detection device in accordance with an exemplary embodiment of the present invention.

In order to eliminate movement caused by hand tremors, the living organism detection device 200 may be mounted to a stabilizing device such as a photographer's tripod, monopod, suction cap, adhesive tape, or a similar mounting and stabilizing device (not shown in the Figures). Alternatively, as shown in FIG. 9, a monopole 910 connected to the living organism detection device 900 with a self-aligned bracket 920 may be used. The adjustable bracket 920 may be of the folding type, the rotating type, or the spring-loaded type. The use of the monopole 910 with the adjustable bracket 920 allows a user to place the device quickly and securely against a partition with just one hand, leaving the other hand free for other activities, such as holding a firearm. Alternatively, the detection device 200 can be slidably mounted to a linear bearing slide and rail device, such as that manufactured by 80/20, Inc. of Columbia City, Ind. (not shown in the Figures). This type of slide and rail device can be temporarily attached to a wall by, for instance, the use of suction cups. Such a configuration would allow a user to linearly move the living organism detection device 200 along the structure S being tested and take several readings. Although it is preferable that the mounting devices described above be utilized with the living organism detection device 200, other mounting and stabilizing devices and means may be employed.

The visual display 222, which is controlled by the microprocessor 206, provides for a display of the output signals and/or data indicative of the absence or presence of living organism in a structure S, or on the other side of the structure S, wall or partition, as desired. The visual display 222 is preferably simple LED indicators (e.g., one indicator for each channel), but other visual display means, including, but not limited to, an LCD display, are available. Alternatively, the visual display 222 need not be utilized. The control interface 220, which is controlled by the microprocessor, provides for an interface between an operator and the living organism detection device 200. The control interface 220 may include, but is not limited to, a power switch, volume and sensitivity controls, and an earphone plug (not shown in FIG. 4). The communication port 226, which is controlled by the microprocessor 206, allows for the signal data processed and analyzed by the living organism detection device 200 to be transferred to a personal computer or a personal digital assistant (PDA). The communication port 226 is preferably either a wired or wireless universal serial bus (USB) or an RS-232 serial port. Alternatively, other types of communication ports 226 may be utilized.

Figure 5A:
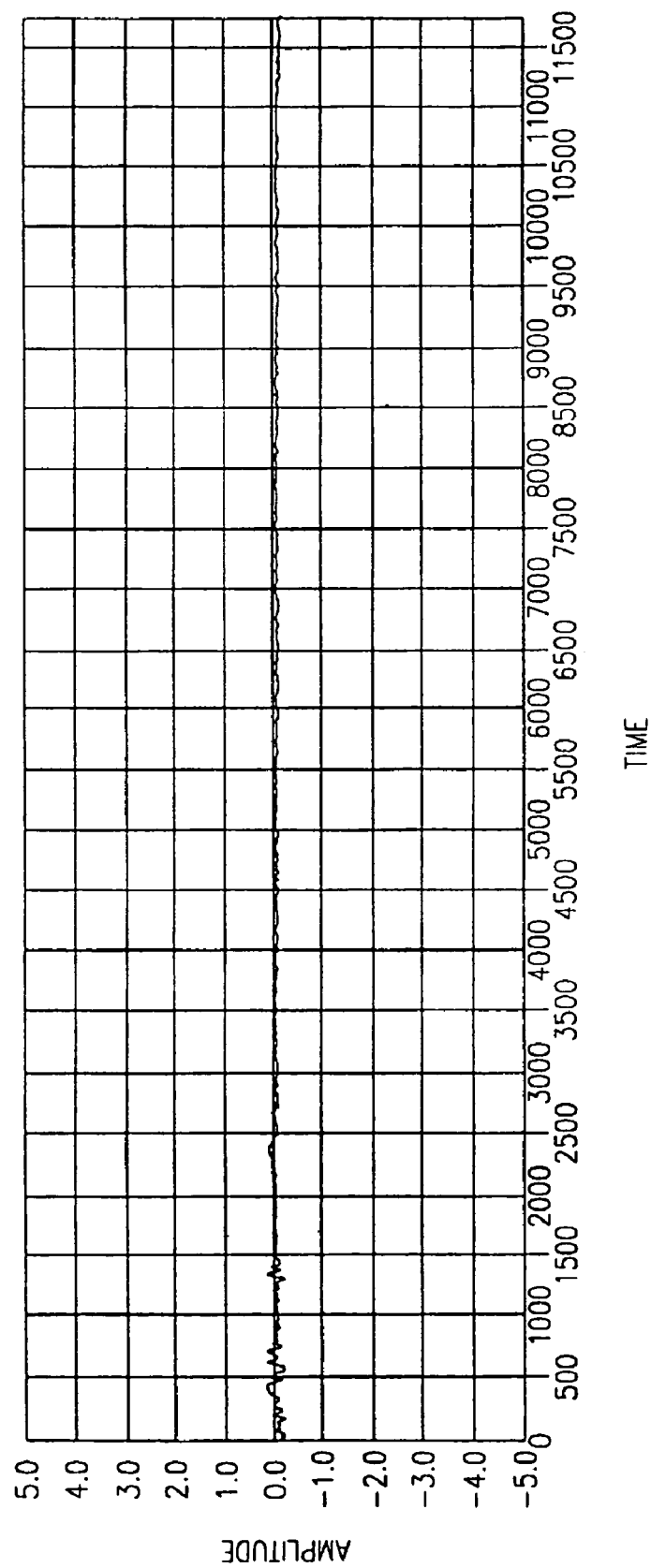
FIG. 5a is a graph of an output signal of the living organism detection device shown in FIG. 4, which shows the absence of insects in a structure.
Figure 5B:
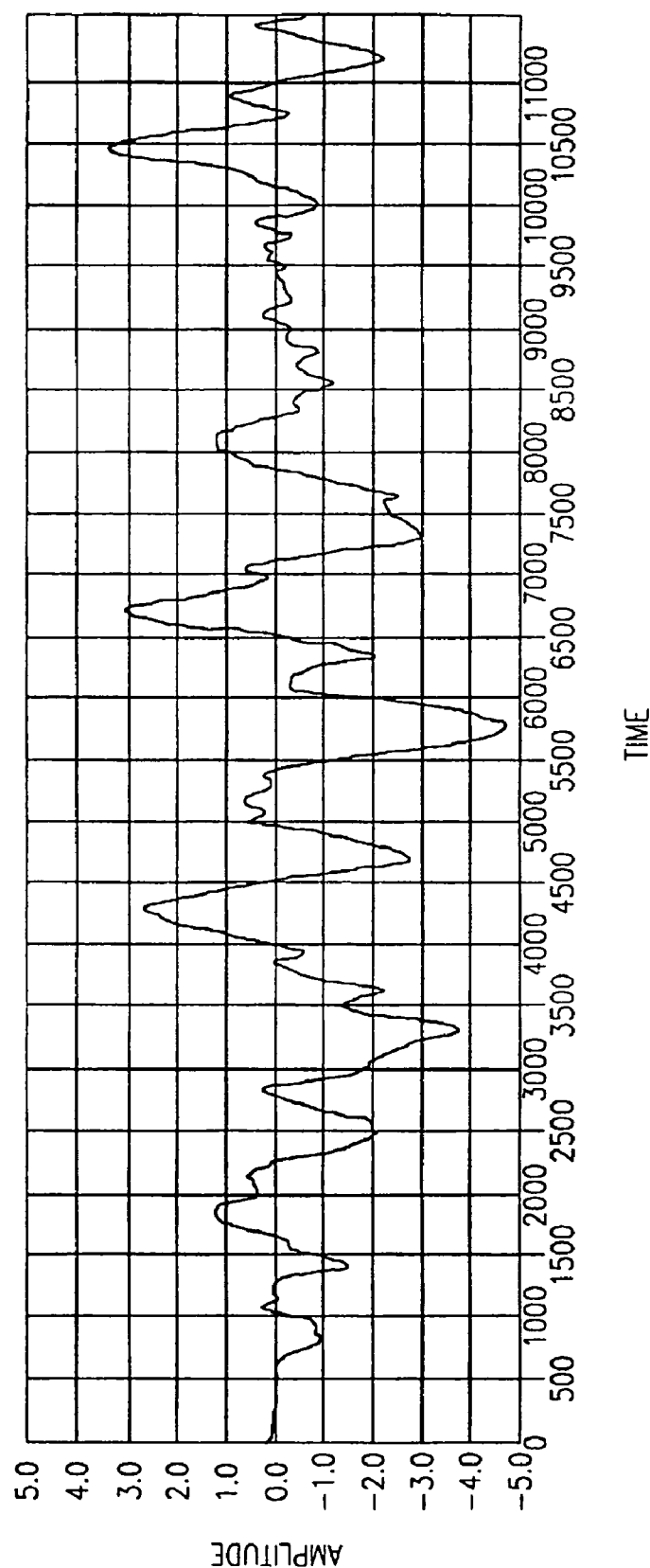
FIG. 5b is a graph of an output signal of the insect detection device shown in FIG. 4, which shows the presence of insects in a structure.

Referring to FIGS. 5a and 5b, an experimental application of the insect detection device 200 was conducted at a residence infested with live termites. The aperture width of each of the antennas 210 was 12.25 mm, while the frequency of each signal generated by each of the transceivers 208 and transmitted by each of the antennas 210 was 24.5 GHz. Therefore, the near field of the signals transmitted by each of the antennas 210 is calculated as approximately 25 mm. The living organism detection device 200 was positioned approximately 30 mm from a wall of the residence, which is clearly outside the near field of the signals transmitted by the antennas 210. A portion of the wall that was known not to contain termites was first tested. In the absence of termites, the output signal generated by the living organism detection device 200 has virtually no amplitude, as shown in FIG. 5a. Next, a portion of the wall that was known to contain live termites was tested. The motion of the termites resulted in output signals having appreciable amplitudes, as shown in FIG. 5b.

The living organism detection device 200 can include a stimulator for stimulating insect movement so as to promote easier detection of insects (not shown in FIG. 4). The stimulator could emit vibrations, ultrasound, heat and/or electromagnetic radiation. Preferably, the stimulator would be used prior to or during the insect detection process.

The living organism detection device 200 may be specifically designed to detect insects in a structure being tested by performing the following steps. First, a plurality of transceivers (such as the transceivers 208) is provided for generating microwave signals and receiving reflected signals from a portion of the structure being tested. Next, each of the transceivers is provided with an antenna (such as the antennas 210) adapted to transmit microwave signals generated by its corresponding transceiver and to receive the reflected signals to be received by its corresponding transceiver. The transceivers are then positioned a pre-selected distance from the portion of the structure being tested, the distance being specifically selected such that the portion of the structure being tested lies within each of the antennas' far field. Next, the transceivers are sequentially activated and sequentially deactivated such that the transceivers are activated and deactivated in succession. The reflected signals received by the transceivers are then processed (for instance, by the microprocessor 206) in order to identify a positive signal that is indicative of the possible presence of insects in the portion of the structure being tested. Finally, all of the reflected signals received by the transceivers are compared to each other in order to determine whether all, or substantially all, of the transceivers have received signals substantially similar to the positive signal to thereby indicate the false presence of insects in the portion of the structure being tested.

As previously referred to, FIG. 6 shows an alternative embodiment where the transceivers 308 and their antennas 310 are enclosed in separate transceiver housings 332 from the living organism detector housing 302. The transceiver housings 332 are connected to the living organism detector housing 302 by one or more cables or a bus 304 that connect the transceivers 308 to the multiplexer 316 and the demultiplexer 314. By separating the transceiver housings 332 from the main living organism detector housing 302, the problems caused by a user handling or shaking the living organism detection device 300 while in operation is eliminated because the transceiver housings 332 can be separately secured to a structure, wall or partition.

Figure 7:
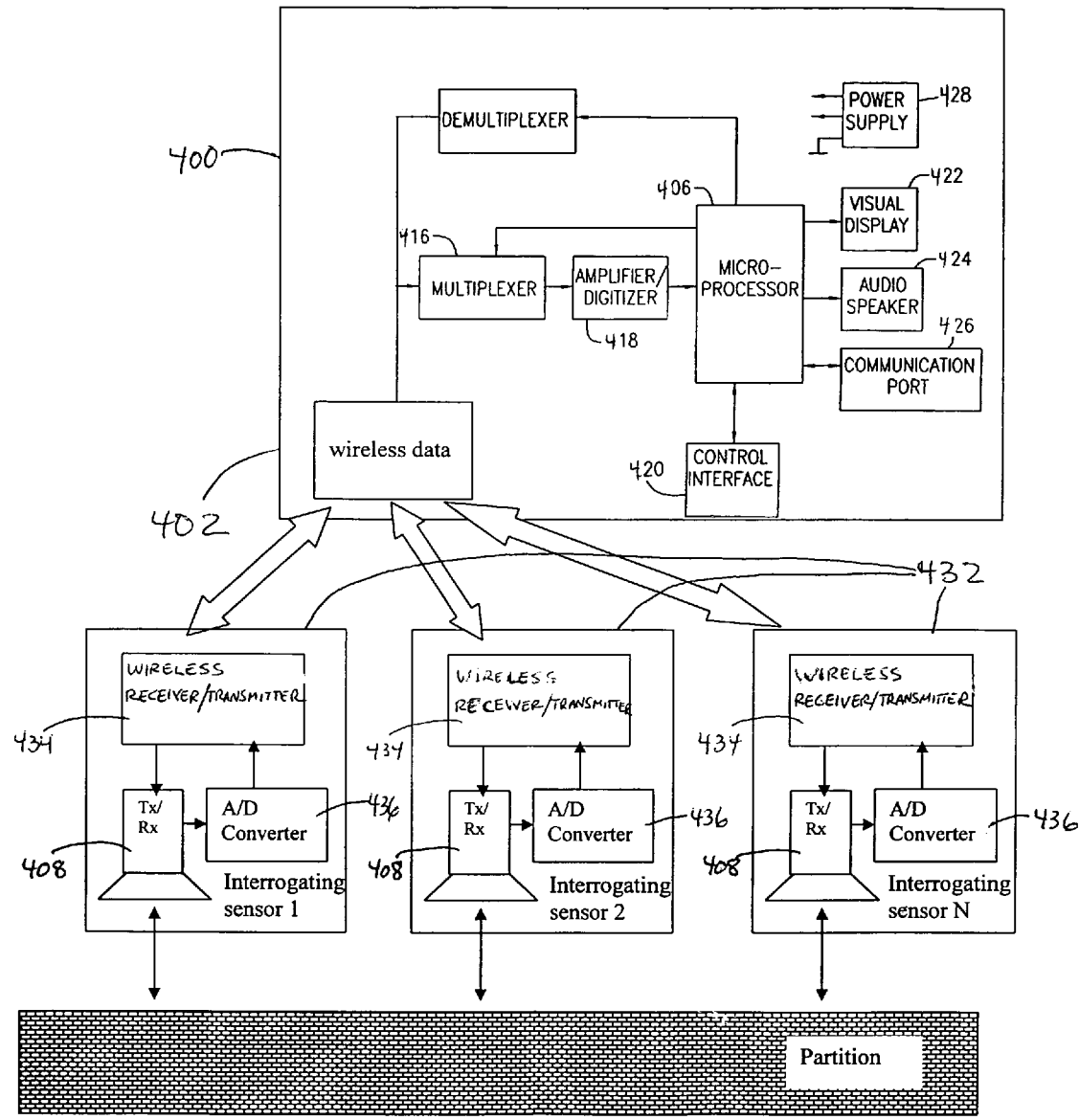
FIG. 7 is a block diagram of a living organism and damage detection device in accordance with a fifth exemplary embodiment of the present invention.
Figure 8:
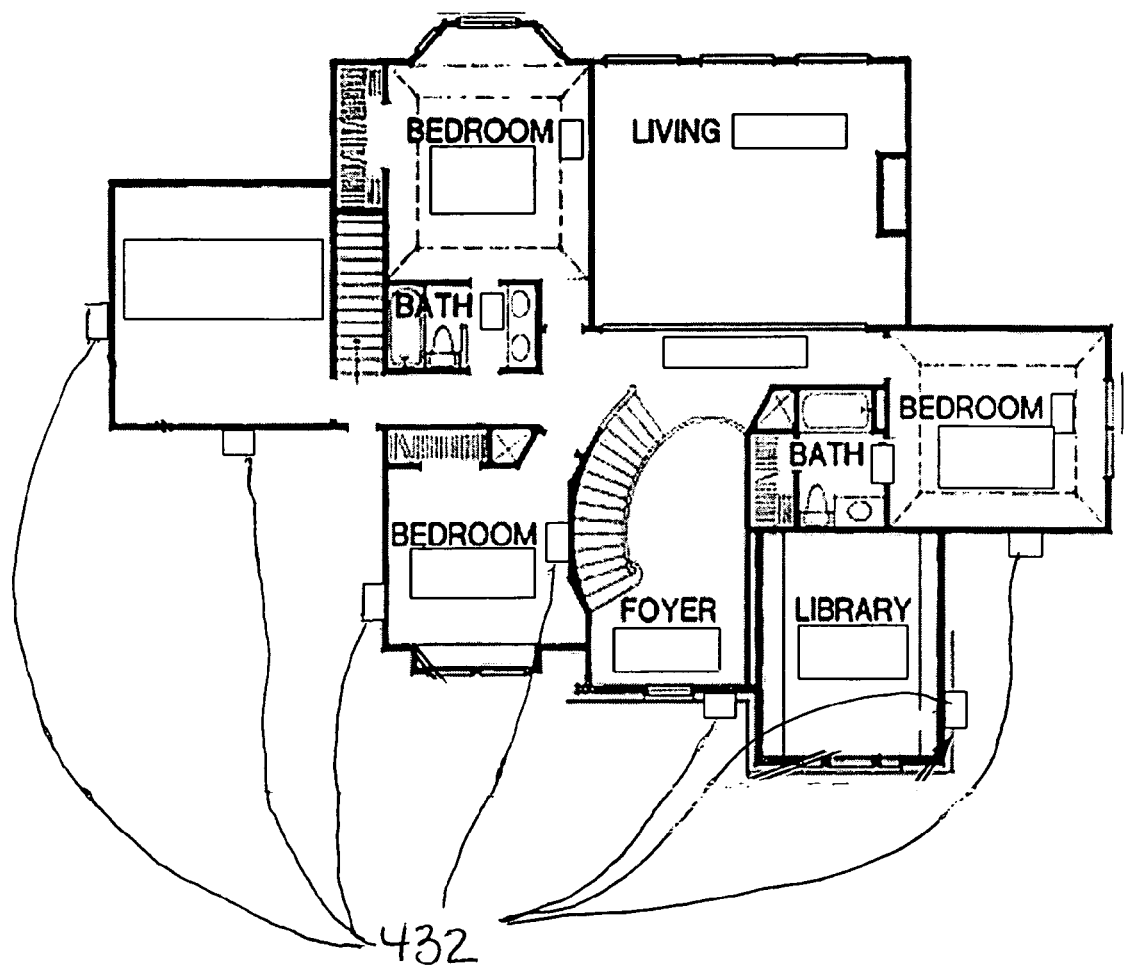
FIG. 8 is a block diagram of a an exemplary application of a living organism and damage detection device in accordance with an exemplary embodiment of the present invention.

Alternatively, as shown in FIG. 7, the transceiver housings 432 can be connected to the main living organism detection device 400 by wireless links. The transceiver housing 432 includes a wireless receiver/transmitter 434 connected to the transceiver 408 which communicates with a wireless receiver/transmitter in the main living organism detector housing 402. Any of known wireless transmission methods may be used, including, but not limited to 802.11x, Bluetooth or analog methods. If a digital transmission method such as 802.11x or Bluetooth is used, an analog-to-digital converter 436 should be used between the transceiver 408 and the wireless receiver/transmitter 434. By using a wireless communication method, the transceiver housings can be attached to a structure, partition or wall using many methods including, but not limited to, manual placement, shot as a projectile, throwing, etc. The wireless communication method is further advantageous because a plurality of transceiver housings 432 can be placed at intervals determined by a user for a particular application. For example, referring to FIG. 8, the transceiver housings 432 can be placed by a police officer at various locations throughout a building to determine the location of an intruder or hostage taker.

A further advantage of using a wireless communication method is that multiple main living organism detection devices 400 can communicate with the transceiver housings 432 at the same time. For example, in the case of police officers isolating an intruder, multiple officers could each have a handheld unit that replicates the main living organism detection device 400. Alternatively, satellite units could simply include a display screen and a wireless receiver such that the main living organism detection device 400 transmits data to the satellite units for display. The use of simple satellite units is an economical solution due to the simplicity of the satellite units.

Any of the embodiments described herein can be modified to address over-the-range rejections. A two-step approach can be used. Since there are very limited types of structures or partitions (concrete, adobe, cement block, brick, and very light partitions (drywall and wood product walls), each type of structure or partition, utilizing a reference thickness, will be calibrated for RF transmission loss to determine the sensitivity threshold for over-the-range rejection. A selector switch can be provided to allow an operator to manually set the detection device for a particular type of structure or partition. The reference threshold for the chosen type of structure or partition can then further be adjusted for the actual type of structure or partition thickness using an ultrasonic thickness gauge built into the detection device. Ultrasonic thickness gauges are commonly used for nondestructive testing (NDT) of materials and structures. Ultrasonic thickness gauges may use time-of-fly measurements to determine thickness of material with known speed of sound. Sound speed data for selected structures or partitions may be stored in the system to be used for calculation of the actual thickness of the particular structure or partition. The thickness data can be used for an automatic correction of the reference sensitivity threshold for over the range rejection.

It should be understood that the embodiments described herein are merely exemplary and that a person skilled in the art may make many variations and modifications without departing from the spirit and scope of the invention. Accordingly, all such variations and modifications are intended to be included within the scope of the invention as defined in the appended claims.

The invention claimed is:

1. A device for detecting the presence of living organisms through a structure, wall or partition, comprising:
   a plurality of transceivers, each of the plurality of transceivers generating interrogating signals and receiving reflected signals from living organisms through a structure, wall, or partition;
   processing means for processing the reflected signals received by each of the plurality of transceivers so as to provide output signals that indicate the presence or absence of living organisms through the structure, wall or partition being tested; and
   a proximity switch to detect the possible presence of a living organism within range of the device, whereby the interrogating signals are not generated until the proximity switch is activated.

2. A device for detecting the presence of living organisms through a structure, wall or partition, comprising:
   a plurality of transceivers, each of the plurality of transceivers generating interrogating signals and receiving reflected signals from living organisms through a structure, wall, or partition;
   processing means for processing the reflected signals received by each of the plurality of transceivers so as to provide output signals that indicate the presence or absence of living organisms through the structure, wall or partition being tested; and
   an ultrasonic thickness gauge.

3. A device for detecting the presence of living organisms through a structure, wall or partition, comprising:
   a plurality of transceivers, each of the plurality of transceivers generating interrogating signals and receiving reflected signals from living organisms through a structure, wall, or partition;
   processing means for processing the reflected signals received by each of the plurality of transceivers so as to provide output signals that indicate the presence or absence of living organisms through the structure, wall or partition being tested; and
   a switch for selecting the type of material that the structure, wall or partition is constructed of.

4. The device as claimed in claim 3, wherein the transceivers include antennas with electromagnetic impedance matched to the electromagnetic impedance of the structure, wall or partition.

5. A method for determining the sensitivity threshold for over the range rejections in a device for detecting the presence of living organisms through a structure, wall or partition, comprising the steps of:
   determining the type of material that the structure, wall or partition is primarily constructed of;
   utilizing a selector switch on the device to set the type material;
   determining the thickness of the structure, wall or partition; automatically adjusting a reference sensitivity threshold based upon the type of material and thickness.

6. The method as claimed in claim 5, whereby the thickness of the structure, wall or partition is measured using an ultrasonic thickness gauge.

* * * * *